United States Patent [19]
Lockerbie et al.

[11] Patent Number: 5,795,735
[45] Date of Patent: Aug. 18, 1998

[54] ISOLATED POLYNUCLEOTIDES ENCODING PKA-BINDING PROTEINS AND METHODS OF PRODUCING THE PROTEINS RECOMBINANTLY

[75] Inventors: Robert Owen Lockerbie, Kirkland; Adam Kashishian, Mountlake Terrace, both of Wash.

[73] Assignee: ICOS Corporation, Bothell, Wash.

[21] Appl. No.: 503,172

[22] Filed: Jul. 17, 1995

[51] Int. Cl.$^6$ .......................... C07K 14/435; C12N 1/21; C12N 15/12
[52] U.S. Cl. .......................... 435/69.1; 536/23.1; 536/23.5; 536/24.3; 435/320.1; 435/326; 435/172.3; 435/252.3
[58] Field of Search .......................... 536/23.1, 23.5, 536/24.3; 435/320.1, 326, 69.1, 172.3, 252.3

[56] References Cited

U.S. PATENT DOCUMENTS

| | | | |
|---|---|---|---|
| 4,568,649 | 2/1986 | Bertoglio-Matte | 436/534 |
| 4,766,046 | 8/1988 | Abra et al. | 424/450 |
| 5,169,637 | 12/1992 | Lenk et al. | 424/450 |
| 5,180,713 | 1/1993 | Abra | 514/31 |
| 5,185,154 | 2/1993 | Lasic et al. | 424/450 |
| 5,204,112 | 4/1993 | Hope et al. | 424/450 |
| 5,252,263 | 10/1993 | Hope et al. | 264/4.3 |
| 5,283,173 | 2/1994 | Fields et al. | 435/6 |

FOREIGN PATENT DOCUMENTS

| | | |
|---|---|---|
| WO 91/16457 | 10/1991 | WIPO. |
| WO 92/02244 | 2/1992 | WIPO. |

OTHER PUBLICATIONS

Kuroda et al. Cell 66:935–947, 1991.
Lin et al. J. Biol. Chem. 270:27804–27811, 1995.
Trendelenburg et al. Biochem. Biophys. Res. Commun. 225:313–319, 1996.
Aldape et al., "Charged Surface Residues of FKBP12 Participate in Formation of the FKBP12–FK506–Calcineurin Complex*", *J. Biol. Chem.* 267:16029–16032 (1992).
Allen et al., "Cyclosporin: A Therapy for Wegner's Granulomatosis" in *ANCA–Associated Vasculitides: Immunological and Clinical Aspects*, Gross (ed.) New York: Plenum Press (1993), pp. 473–476.
Belldegrun et al., "Interferon–α Primed Tumor–Infiltrating Lymphocytes Combined with Interleukin–2 and Interferon–α as Therapy for Metastatic Renal Cell Carcinoma", *J. Urol.* 150:1384–1390 (1993).
Boudet et al., "UV–treated polystyrene microtitre plates for use in an ELISA to measure antibodies aginst synthetic peptides" *J.Immunol.Meth.* 142:73–82 (1991).
Bougneres et al., "Factors Associated With Early Remission Of Type I Diabetes In Children Treated With Cyclosporine", *N.Eng.J.Med.* 318:663–670 (1988).
Bougneres et al., "Limited Duration of Remission of Insulin Dependency in Children with Recent Overt Type I Diabetes Treated with Low–Dose Cyclosporin", *Diabetes* 39:1264–1272 (1990).

Bregman et al., "Molecular Characterization of Bovine Brain P75, a High Affinity Binding Protein for the Regulatory Subunit of cAMP–dependent Protein Kinase IIβ*", *J.Biol.Chem.* 266:7202–7213 (1991).
Bruton and Koeller, "Recombinant Interleukin–2", *Pharmacotherapy* 14:635–656 (1994).
Brynskov, "Cyclosporin in Crohn's disease", *Dan.Med.Bull.* 41:332–344 (1994).
Carr et al., "Follicle–stimulating Hormone Regulation of A–kinase Anchoring Proteins in Granulosa Cells*", *J.Biol.Chem.* 268:20729–20732 (1993).
Carr et al., "Association of the type II cAMP–dependent Protein Kinase with a Human Thyroid RII–anchoring Protein", *J.Biol.Chem.* 267:13376–13382 (1992).
Carr and Scott, "Blotting and band–shifting: techniques for studying protein–protein interactions", *T.I.B.S.* 17:246–249 (1992).
Carr et al., "Interaction of the Regulatory Subunit (RII) of cAMP–dependent Protein Kinase with RII–anchoring Proteins Occurs through an Amphipathic Helix Binding Motif*", *J.Biol.Chem.* 266:14188–14192 (1991).
Carr et al., "Localization of the cAMP–dependent Protein Kinase to the Postsynaptic Densities by A–Kinase Anchoring Proteins", *J.Biol.Chem.* 267:16816–16823 (1992).
Cheley et al., "Type II Regulatory Subunits of cAMP–dependent Protein Kinase and Their Binding Proteins in the Nervous System of *Aplysia californica*", *J.Biol.Chem.* 269:2911–2920 (1994).
Choi and Targan, "Immunomodulator Therapy in Inflammatory Bowel Disease", *Dig.Dis and Sci.* 39:1885–1892 (1994).
Clipstone and Crabtree, "Identification of calcineurin as a key signalling enzyme in T–lymphocyte activation", *Nature* 357:695–697 (1992).
Coghlan et al., "A–Kinase Anchoring Proteins: a key to selective activation of cAMP–responsive events?", *Mol. Cell.Biochem.* 127:309–319 (1993).
Coghlan et al., "Cloning and Characterization of AKAP 95, a Nuclear Protein That Associates with the Regulatory Subunit of Type II cAMP–dependent Protein Kinase*", *J.Biol.Chem.* 269:7658–7665 (1994).
Cooper et al., "Atopic Dermatitis: Recent Trends in Pathogenesis and Therapy", *J.Invest.Derm* 102:128–137 (1994).
Cuéllar et al., "Treatment of psoriatic arthritis", *Balliere's Clin.Rheum.* 8:483–498 (1994).
Cyert and Thorner, "Calcineurin–like Activity in *Saccharomyces cerevisiae*", *J.Cell.Biol.* 107:841a (1989).
de Groen et al., "Central Nervous System Toxicity After Liver Transplantation", *N.Eng.J.Med.* 317:861–866 (1987).

(List continued on next page.)

*Primary Examiner*—Elizabeth C. Kemmerer
*Attorney, Agent, or Firm*—Marshall, O'Toole, Gerstein, Murray & Borun

[57] ABSTRACT

The present invention provides novel PKA-binding polypeptides, nucleic acids that encode the polypeptides and antibodies specifically immunoreactive with the polypeptides.

10 Claims, No Drawings

OTHER PUBLICATIONS

DeCamilli et al., "Heterogeneous Distribution of the cAMP Receptor Protein RII in the Nervous System: Evidence for Its Intracellular Accumulation of Microtubules, Microtubule– organizing Centers, and in the Area of the Golgi Complex", *J.Cell.Biol.* 103:189–203 (1986).

Deeg et al., "Cyclosporine as Prophylaxis for Graft–Versus–Host Disease: A Randomized Study in Patients Undergoing Marrow Transplantation for Acute Nonlymphoblastic Leukemia", *Blood* 65:1325–1334 (1985).

Dillman, "The Clinical Experience with Interleukin–2 in Cancer Therapy", *Cancer Biotherapy* 9:183–209 (1994).

Dougados and Torley, "Efficacy of Cyclosproin A in Rheumatoid Arthritis: Worldwide Experience", *Br.J.Rheum* 32(suppl 1):57–59 (1993).

Durfee et al., "The retinoblastoma protein associates with the protein phosphatase type 1 catalytic subunit", *Genes and Development* 7:555–567 (1993).

Eichholtz et al., "A Myristoylated Pseudosubstrate Peptide, a Novel Protein Kinase C Inhibitor*", *J.Biol.Chem* 268:1982–1986 (1993).

Eidelman et al., "Neurologic Complications of FK 506", *Transplnt.Proc.* 23:3175–3178 (1991).

Elliot and Chase, "Prevention or delay of Type 1 (insulin–dependent) diabetes mellitus in children using nicotinamide", *Diabetologia* 34:362–365 (1991).

Ellis et al., "Cyclosporine Improves Psoriasis in a Double-blind Study", *JAMA* 256:3110–3116 (1986).

Feldt–Rasmussen et al., "Oral cyclosporine for severe chronic idiopathic urticaria and angioedema", *Diabetes Medicine* 7:429–433 (1990).

Feutren, "Renal Morphology Afteer Cyclosporin A Therapy In Rheumatoid Arthritis Pateints," *Br.J.Rheum.* 32(suppl 1):65–71 (1993).

Feutren et al., "Cyclosporin Increases The Rate And Length Of Remissions In Insulin–Dependent Diabetes Of Recent Onset", *Lancet* 2:119–124 (1986).

Førre et al., "An Open, Controlled, Randomized Comparison Of Cyclosporine And Azathioprine In The Treatment Of Rheumatoid Arthritis: A Preliminary Report", *Arthritis Reheum.* 30:88–92 (1987).

Figlin et al., "Session II" AIDS/Cancer Therapies, *Seminars in Hematology,* 29(suppl 1):33–35 (1992).

Fradin et al., "Oral cyclosporine for severe chronic idiopathic urticaria and angioedema", *J.Am.Acad.Derm.* 25:1065–1067 (1991).

Fung et al., "Adverse Effects Associated With the Use of FK 506", *Transplant.Proc.* 23:3105–3108 (1991).

Glantz et al., "cAMP Signaling in Neurons: Patterns of Neuronal Expression and Intracellular Localization for a Novel Protein, AKAP 150, that Anchors the Regulatory Subunit of cAMP–Dependent Protein Kinase IIβ", *Mol. Cell.Biol.* 3:1215–1228 (1992).

Glantz et al., "Characterization of Distinct Tethering and Intracellular Targeting Domains in AKAP75 a Protein That Links cAMP–dependent Protein Kinase IIβ to the Cytoskeleton*", *J.Biol.Chem.* 268:12796–12804 (1993).

Greengard et al., "Enhancement of the Glutamate Response by cAMP–Dependent Protein Kinase in Hippocampal Neurons", *Science* 253:1135–1138 (1991).

Guerini and Klee, "Cloning of human calcineurin A: Evidence for two isozymes and identification of a polyproline structural domain", *Proc.Natl.Acad.Sci.(USA)* 86:9183–9187 (1989).

Harlow and Lane, "Immunoaffinity Purification of Antibodies on an Antigen Column", in *Antibodies: A Laboratory Manual,* Harlow and Lane (eds.) Cold Spring Harbor Laboratory:Cold Spring Harbor, NY (1988), pp. 313–318.

Hashimoto et al., "Identification of an Autoinhibitory Domain in Calcineurin*", *J.Biol.Chem.* 265:1924–1927 (1990).

Hathaway et al., "Interaction of Calmodulin with Myosin Light Chain Kinase and cAMP–dependent Protein Kinase in Bovine Brain*", *J.Biol.Chem.* 265:8183–8189 (1981).

Hausken et al., "Type II Regulatory Subunit (RII) of the cAMP–dependent Protein Kinase Interaction with A–kinase Anchor Proteins Requires Isoleucines 3 and 5*", *J.Biol.Chem.* 269:24245–24251 (1994).

Hirsch et al., "Cloning and Expression of an Intron–less Gene for AKAP 75, an Anchor Protein for the Regulatory Subunit of cAMP–dependent Protein Kinase IIβ*", *J.Biol.Chem.* 267:2131–2134 (1992).

Hubbard and Cohen, "On target with a new mechanism for the regulation of protein phosphorylation", *T.I.B.S.* 17:172–177 (1993).

Hulton et al., "Long–term cyclosporin A treatment of minimal–change nephrotic syndrome of childhood", *Pediatr. Nephrol.* 8:401–403 (1994).

Jain et al., "The T–cell transcription factor $NFAT_p$ is a substrate for calcineurin and interacts with Fos and Jun", *Nature* 365:352–355 (1993).

Jenner et al., "Cyclosporin A treatment of young children with newly–diagnosed Type 1 (insulin–dependent) diabetic mellitus", *Diabetiologia* 35:884–888 (1992).

Kahan, "Cyclosporine", *N.Eng.J.Med.* 321:1725–1738 (1989).

Kahan et al., "Complications of Cyclosporine–Prednisone Immunosuppression in 402 Renal Allograft Recipients Exclusively Followed At A Single Center For From One To Five Years", *Transplantation* 43:197–204 (1987).

Kaplan, "Recent Advances in Cytokine Therapy in Leprosy", *J.Infect.Dis.* 167(suppl 1):S18–22 (1993).

Kay, "Immunosuppressive Agents in Chronic Severe Asthma", *Allergy Proc.* 15(3):147–150 (1994).

Keegan et al., "Separation of DNA Binding from the Transcription–Activating Function of a Eukaryotic Regulatory Protein", *Science* 231:699–704 (1986).

Keryer et al., "A High–Affinity Binding Protein for the Regulatory Subunit of cAMP–Dependent Protein Kinase II in the Centrosome of Human Cells", *Exp.Cell Res.* 204:230–240 (1993).

Klee et al., "Calcineurin", *Adv.Enzymol.* 61:149–200 (1984).

Lange and Reiderer, "Glutamatergic Drugs in Parkinson's Disease", *Life Sciences* 55:2067–2075 (1994).

Leaker and Cairns, "Clinical aspects of cyclosporin nephrotoxicity", *Br.J.Hosp.Med.* 52:520–534 (1994).

Lockerbie et al., "Anchoring of protein kinase A is required for mediating the inhibitory effects of 3',5'–cyclic adenosine monophosphate on IL–2 transcription in human T cells" *J.Cell Biochem.* Suppl.21A:76 Abstract D2155 (1995).

Ludwin and Alexopolulou, "Cyclosporin A Nephropathy in Patients with Rheumatoid Arthritis", *Br. J.Rheum.* 32(suppl 1):60–64 (1993).

Ma and Ptashne, "Deletion Analysis of GAL4 Defines Two Transcriptional Activating Segments", *Cell* 48:847–853 (1987).

MacFarlane et al., "The Hematologic Toxicity of Interleukin–2 in Patients with Metastatic Melanoma and Renal Cell Carcinoma", *Cancer* 75:1030–1037 (1995).

Manev et al., "Macrolide antibiotics protect neurons in culture against the N-methyl-D-aspartate (NMDA) receptor-mediated toxicity of glutamate", *Brain Res.* 624:331–335 (1993).

Martin et al., "Follow-up of cyclosporin A treatment in Type 1 (insulin-dependent) diabetes mellitus: lack of long-term effects", *Dibetologia* 34:429–434 (1991).

Mason, "Pharmacology of Cyclosporine (Sandimmune) VII. Pathophysiology and Toxicology of Cyclosporine in Humans and Animals", *Pharmacol.Rev.* 42:423–434 (1989).

McCartney et al., "Cloning and Characterization of A-kinase Anchor Protein 100 (AKAP100)", *J.Biol. Chem.* 270:9327–9333 (1995).

McCauley et al., "The nephrotoxicity of FK506 as compared with cyclosporine", *Curr.Opin.Nephrol.Hyperten.* 2:662–669 (1993).

Meldrum, "The role of glutamate in epilepsy and other CNS disorders", *Neurology* 44(suppl 8):S14–S23 (1994).

Merchant et al., "Immunotherapy for malignant glioma using human recombinant Interleukin-2 and activated autologous lymphocytes", *J.Neuro.* 8:173–188 (1990).

Meyrier, "Treatment of nephrotic syndrome with cyclosporin A. What remains in 1994?", *Nephrol.Dial. Transplant* 9:596–598 (1994).

Morris, "New Small Molecule Immunosuppressants for Transplantation: Review of Essential Concepts", *J.Heart and Lung Transplant.* (Nov./Dec.) pp. S275–S285 (1993).

Najarian et al., "A Single Institution, Randomized, Prospective Trial of Cyclosporine Versus Azathioprine–Antilymphocyte Globulin for Immunosuppression in Renal Allograft Recipients", *Ann.Surg.* 201:142–157 (1985).

Ngai et al., "Protein A antibody–capture ELISA (PACE): an ELISA format to avoid denaturation of surface–adsorbed antigens" *J.Immunol.Meth.* 158:267–276 (1993).

Nussenblatt et al., Cyclosporin A Therapy in the Treatment of Intraocular Inflammatory Disease Resistant to Systemic Corticosteroids and Cytotoxic Agents, *Am.J.Ophthalmol.* 96:275–282 (1983).

Obar et al., "The RII Subunit of cAMP–Dependent Protein Kinase Binds to a Common Amino–Terminal Domain in Microtubule–Associated Proteins 2A, 2B, and 2C", *Neuron*, 3:639–645 (1989).

O'Keefe et al., "FK–506– and CsA–sensitive activation of the interleukin–2 promoter by calcineurin", *Nature* 357:692–694 (1992).

Olney, "Excitatory Transmitter Neurotoxicity", *Neurobiology of Aging* 15:259–260 (1994).

Oyer et al., "Cyclosporine in Cardiac Transplantation: A 2½ Year Follow-Up", *Transplant Proc.* 15:Supp 1:2546–2552 (1983).

Pacor et al., "Cyclosporin in Behcet's Disease: Results in 16 Patients after 24 Months of Therapy", *Clin Rheum.* 13:224–227 (1994).

Perrino et al., "Characterization of the Phosphatase Activity of a Baculovirus–expressed Calcineurin A Isoform*", *J.Biol.Chem.* 267:15965–15969 (1992).

Peters et al., "Tacrolimus A Review of its Pharmacology, and Therapeutic Potential in Hepatic and Renal Transplantation", *Drugs* 4:746–794 (1993).

Pierce et al., "Cellular Therapy: Scientific Rationale and Clinical Results in the Treatment of Metastatic Renal–Cell Carcinoma", *Sem. Oncol.* 22:74–80 (1995).

Platz et al., "Nephrotoxicity Following Orthotopic Liver Transplantation", *Transplantation* 58:170–178 (1994).

Pruslin et al., "Caveats and suggestions for the ELISA" *J.Immunol.Meth.* 137:27–35 (1991).

Reece et al., "Neurologic complications in allogeneic bone marrow transplant patients receiving cyclosporin", *Bone Marrow Transplant.* 8:393–401 (1991).

Reitamo and Granlund, "Cyclosporin A in the treatment of chronic dermatitis of the hands", *Br.J.Derm.* 130:75–78 (1994).

Rios et al., "Identification of a high affinity binding protein for the regulatory subunit RII$\beta$ of cAMP–dependent protein kinase in Golgi enriched membranes of human lymphoblasts", *EMBO J.* 11:1723–1731 (1992).

Rosenmund et al., "Anchoring of protein kinase A is required for modulation of AMPA/kainate receptors on hippocampal neurons", *Nature* 368:853–856 (1994).

Rubino et al., "Localization and Characterization of the Binding Site for the Regulation Subunit of Type II cAMP–Dependent Protein Kinase on MAP2", *Neuron* 3:631–638 (1989).

Ryffel, "Pharmacology of Cyclosporine VI. Cellular Activation: Regulation of Intracellular Events by Cyclosporine", *Pharm.Rev.* 41:407–422 (1989).

Salek et al., "Cyclosporin greatly improves the quality of life of adults with severe atopic dermatitis. A randomized, double–blind, placebo–controlled trial", *Br.J.Derm.* 129:422–430 (1993).

Sánchez et al., "Immune Responsiveness and Lymphokine Production in Patients with Tuberculosis and Healthy Controls", *Inf.Immunol.* 62:5673–5678 (1994).

Schreiber, "Chemistry and Biology of the Immunophilins and Their Immunosuppressive Ligands", *Science* 251:283–287 (1991).

Schreiber and Crabtree, "The mechanism of action of cyclosporin A and FK506", *Immunol. Today* 13:136–142 (1992).

Schultz et al., "Cyclosporin A Therapy of Immune–Mediated Thrombocytopenia in Children" *Blood* 85:1406–1408 (1995).

Scott, "Cyclic Nucleotide–Dependent Protein Kinases" *Pharm.Ther.* 50:123–145 (1991).

Scott and Carr, "Subcellular Localization of the Type II cAMP–Dependent Protein Kinase", *N.I.P.S.* 7:143–148 (1992).

Scott et al., "Identification of an inhibitory region of the heat–stable protein inhibitor of the cAMP–dependent protein kinase", *Proc.Natl.Acad.Sci.(USA)* 82:4379–4383 (1985).

Scott and McCartney, "Localization of A–kinase through Anchoring Proteins", *Mol.Endocrinol.* 8:5–11 (1994).

Sharma et al., "Which way for drug–mediated immunosuppression?", *Curr.Opin.Immunol.* 6:784–790 (1994).

Shimizu et al., "Acute leucoencephalopathy during cyclosporin A therapy in a patient with nephrotic syndrome", *Pediatr.Nephrol.* 8:483–485 (1994).

Showstack et al., "The Effect of Cyclosporine of the Use of Hospital Resources for Kidney Transplantation", *N.Eng.J.Med.* 321:1086–1092 (1989).

Sinclair, "A Randomized Clinical Trial Of Cyclosporine In Cadaveric Renal Transplantation", *N.Eng.J.Med.* 314:1219–1225 (1986).

Skålhegg et al., "Location of cAMP–Dependent Protein Kinase Type with the TCR–CD3 Complex", *Science* 263:84–87 (1994).

Spencer et al., "Controlling Signal Transduction with Synthetic Ligands", *Science* 262:1019–1024 (1993).

Starzl et al., "Liver Transplantation With Use of Cyclosporin A and Prednisone", *N.Eng.J.Med.* 305:266–269 (1981).

Stewart and Young, "Laboratory Techniques in Solid Phase Peptide Synthesis", *Solid Phase Peptide Synthesis*, 2nd Edition.

Stofko–Hahn, "A single step purification for recombinant proteins, Characterization of a microtubule associated protein (MAP 2) fragment which associates with the type II cAMP–dependent protein kinase", *F.E.B.S. Letts.* 302:274–278 (1992).

Sturrock et al., "Acute haemodynamic and renal effects of cyclosporin and indomethacin in man", *Nephrol.Diag.Transplant* 9:1149–1156 (1994).

Svarstad et al., "Renal effects of maintenance low–dose cyclosporin A treatment in psoriasis", *Nephrol.Dial.Transplant* 9:1462–1467 (1994).

Tam et al., "$S_N2$ Deprotection of Synthetic Peptides with a Low Concentration of HF in Dimethyl Sulfide: Evidence and Application in Peptide Synthesis[1]", *J.Am.Chem.Soc.* 105:6442–6455 (1983).

Tejani et al., "Cyclosporine (CY) Induced Remission of Relapsing Nephrotic Syndrome (RNS) In Children", *Kidney Intl.* 29:206 (1986).

Theurkauf and Vallee, "Molecular Characterization of the cAMP–dependent Protein Kinase Bound to Microtubule–associated Protein 2*", *J.Biol.Chem.* 257:3284–3290 (1982).

Thomson and Starlz, "New Immunosuppressive Drugs: Mechanistic Insights and Potential Therapeutic Advances", *Immunol.Rev.* 136:71–98 (1993).

Thomason et al., "The Periodontal Problems and Management of the Renal Transplant Patient", *Renal Failure* 16:731–745 (1994).

Tokuda et al., "Effect of Low–Dose Cyclosporin A on Systemic Lupus Erythematosus Disease Activity", *Arth.Rheumat.* 37:551–0558 (1994).

Toronto Lung Transplant, "Experience With Single–Lung Transplantation for Pulmonary Fibrosis", *JAMA* 259:2258–2262 (1988).

Undenfriend et al., "Scintillation proximity radioimmunoassay utilizing $^{125}I$–labeled ligands", *PNAS (USA)* 82:8672–8676 (1985).

Undenfriend et al., "Scintillation Proximity Assay: A Sensitive and Continuous Isotopic Method for Monitoring Ligand/Receptor and Antigen/Antibody Interactions*", *Anal.Biochem.* 161:494–500 (1987).

Van Joost et al., "Cyclosporin in atopic dermatitis" a multicentre placebo–controlled study, *Br.J.Derm.* 130:634–640 (1994).

Vogelzang et al., "Subcutaneous Interleukin–2 Plus Interferon Alfa–2a in Metastatic Renal Cancer: An Outpatient Multicenter Trial", *J.Clin.Oncol.* 11:1809–1816 (1993).

Vojtek et al., "Mammalian Ras Interacts Directly with the Serine/Threonine Kinase Raf", *Cell* 74:205–214 (1993).

Walsh et al., "An Adenosine 3',5'–Monophosphate–dependent Protein Kinase from Rabbit Skeletal Muscle*", *J.Biol.Chem.* 243:3763–3765 (1969).

Wang et al., "Regulation of Kainate Receptors by cAMP–Dependent Protein Kinase and Phosphatases", *Science* 253:1132–1135 (1991).

Weiss and Littman, "Signal Transduction by Lymphocyte Antigen Receptors", *Cell* 76:263–274 (1994).

Wells and Tugwell, "Cyclosporin A in Rheumatoid Arthritis" Overview of Efficacy, *Br.J.Rheum.* 32(suppl 1):51–56 (1993).

Whittington et al., "Interleukin–2 A Review of its Pharmacological Properties and Therapeutic Use in Patients with Cancer", *Drugs* 46(3):447–515.

Wilson et al., "Sensorimotor neuropathy resembling CIDP in patients receiving FK506", *Muscle and Nerve* 17:528–532 (1994).

Young et al., "A prospective study of renal structure and function in psoriasis patients treated with cyclosporin", *Kidney International* 46:1216–1222 (1994).

Author Unknown, "Drugs Used In Transplantation," *Executive Briefing* 15:12–16 (1995).

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
Asp Leu Ile Glu Glu Ala Ala Ser Arg Ile Val Asp Ala Val Ile Glu
1               5                   10                  15
Gln Val Lys Ala Ala Gly Ala
                20
```

( 2 ) INFORMATION FOR SEQ ID NO:2:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Asp Leu Ile Glu Glu Ala Ala Ser Arg Pro Val Asp Ala Val Ile Glu
1               5                   10                  15
Gln Val Lys Ala Ala Gly Ala
                20
```

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

ATTAACCCTC ACTAAAG      17

( 2 ) INFORMATION FOR SEQ ID NO:4:

( i ) SEQUENCE CHARACTERISTICS:
        ( A ) LENGTH: 17 base pairs
        ( B ) TYPE: nucleic acid (C) STRANDEDNESS: single
(D) TOPOLOGY: linear (ii) MOLECULE TYPE: cDNA (xi) SEQUENCE DESCRIPTION: SEQ ID NO:4:

GATATCACTC AGCATAA                                                                                    17

(2) INFORMATION FOR SEQ ID NO:5:

(i) SEQUENCE CHARACTERISTICS:
    (A) LENGTH: 2850 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:5:

| | | | | | | |
|---|---|---|---|---|---|---|
| GGCACGAGGA | GCAGCAGGTG | GAGGCTGGTG | CTGTGCAGCT | GAGGGCTGAC | CCTGCCATCA | 60 |
| AGGAACCTCT | CCCCGTGGAA | GACGTCTGTC | CCAAAGTAGT | GTCCACACCC | CCAGTGTCA | 120 |
| CAGAGCCTCC | AGAAAAGGAA | CTGTCCACCG | TGAGCAAGCT | GCCTGCAGAG | CCCCCAGCAT | 180 |
| TGCTCCAGAC | ACACCCACCT | TGCCGAAGAT | CAGAGTCCTC | GGGCATTCTT | CCTAACACCA | 240 |
| CAGACATGAG | ATTGCGACCA | GGAACACGCA | GAGACGACAG | TACAAAGCTG | GAGCTAGCCC | 300 |
| TGACAGGTGG | TGAAGCCAAA | TCGATTCCTC | TAGAGTGCCC | CCTTTCATCC | CCAAAGGGTG | 360 |
| TACTATTCTC | CAGCAAATCA | GCTGAGGTGT | GTAAGCAAGA | TTCCCCCTTC | AGCAGGGTGC | 420 |
| CAAGGAAGGT | CCAGCCAGGC | TACCCCGTAG | TCCCCGCAGA | GAAGCGTAGC | TCTGGGGAGA | 480 |
| GGGCAAGAGA | GACAGGTGGG | GCCGAAGGGA | CTGGTGATGC | CGTGTTGGGG | GAAAAGGTGC | 540 |
| TTGAAGAAGC | TCTGTTGTCT | CGGGAGCATG | TCTTGGAATT | GGAGAACAGC | AAGGGCCCCA | 600 |
| GCCTGGCCTC | TTTAGAGGGG | GAAGAAGATA | AGGGGAAGAG | CAGCTCATCC | CAGGTTGGTG | 660 |
| GGGCCAGTGC | AGGAGGAAGA | GTATGTAGCA | GAGAAGTTGC | CAAGTAGGTT | CATCGAGTCG | 720 |
| GCTCACACAG | AGCTGGCAAA | GGACGATGCG | GCGCCAGCAC | CCCCAGTCGC | AGACGCCAAA | 780 |
| GCCCAGGACA | GAGGTGTCGA | GGGAGAACTG | GGCAATGAGG | AGAGCTTGGA | TAGAAATGAG | 840 |
| GAGGGCTTGG | ATAGAAATGA | GGAGGGCTTG | GATAGAAATG | AGGAGAGCTT | GGATAGAAAT | 900 |
| GAGGAGGGCT | TGGATAGAAA | TGAGGAGATT | AAGCGGGCTG | CCTTCCAGAT | AATCTCCCAA | 960 |
| GTGATCTCAG | AAGCAACCGA | ACAGGTGCTG | GCCACCACGG | TTGGCAAGGT | TGCAGGTCGT | 1020 |
| GTGTGTCAGG | CCAGTCAGCT | CCAAGGGCAG | AAGGAAGAGA | GCTGTGTCCC | AGTTCACCAG | 1080 |
| AAAACTGTCT | TGGGCCCAGA | CACTGCGGAG | CCTGCCACAG | CAGAGGCAGC | TGTTGCCCCG | 1140 |
| CCGGATGCTG | GCCTCCCCTT | GCCAGGCCTA | CCAGCAGAGG | GCTCACCACC | ACCAAAGACC | 1200 |
| TACGTGAGCT | GCCTGAAGAG | CCTTCTGTCC | AGCCCCACCA | AGGACAGTAA | GCCAAATATC | 1260 |
| TCTGCACACC | ACATCTCCCT | GGCCTCCTGC | CTGGCACTGA | CCACCCCCAG | TGAAGAGTTG | 1320 |
| CCGGACCGGG | CAGGCATCCT | GGTGGAAGAT | GCCACCTGTG | TCACCTGCAT | GTCAGACAGC | 1380 |
| AGCCAAAGTG | TCCCTTTGGT | GGCTTCTCCA | GGACACTGCT | CAGATTCTTT | CAGCACTTCA | 1440 |
| GGGCTTGAAG | ACTCTTGCAC | AGAGACCAGC | TCGAGCCCCA | GGGACAAGGC | CATCACCCCG | 1500 |
| CCACTGCCAG | AAAGTACTGT | GCCCTTCAGC | AATGGGGTGC | TGAAGGGGA | GTTGTCAGAC | 1560 |
| TTGGGGGCTG | AGGATGGATG | GACCATGGAT | GCGGAAGCAG | ATCATTCAGG | AGGTTCTGAC | 1620 |
| AGGAACAGCA | TGGATTCCGT | GGATAGCTGT | TGCAGTCTCA | AGAAGACTGA | GAGCTTCCAA | 1680 |
| AATGCCCAGG | CAGGCTCCAA | CCCTAAGAAG | GTCGACCTCA | TCATCTGGGA | GATCGAGGTG | 1740 |

| | | | | | | |
|---|---|---|---|---|---|---|
| CCAAAGCACT | TAGTCGGTCG | GCTAATTGGC | AAGCAGGGGC | GCTATGTGAG | TTTTCTGAAG | 1800 |
| CAAACATCTG | GTGCCAAGAT | CTACATTTCA | ACCCTGCCTT | ACACCCAGAG | CGTCCAGATC | 1860 |
| TGCCACATAG | AAGGCTCTCA | ACATCATGTA | GACAAAGCGC | TGAACTTGAT | TGGGAAGAAG | 1920 |
| TTCAAAGAGC | TGAACCTCAC | CAATATCTAC | GCTCCCCCAT | TGCCTTCACT | GGCACTGCCT | 1980 |
| TCTCTGCCGA | TGACATCCTG | GCTCATGCTG | CCTGATGGCA | TCACCGTGGA | GGTCATTGTG | 2040 |
| GTCAACCAGG | TCAATGCCGG | GCACCTGTTC | GTGCAGCAGC | ACACACACCC | TACCTTCCAC | 2100 |
| GCGCTGCGCA | GCCTCGACCA | GCAGATGTAC | CTCTGTTACT | CTCAGCCTGG | AATCCCCACC | 2160 |
| TTGCCCACCC | CAGTGGAAAT | AACGGTCATC | TGTGCCGCCC | CTGGTGCGGA | CGGGGCCTGG | 2220 |
| TGGCGAGCCC | AAGTGGTTGC | CTCCTACGAG | GAGACCAACG | AAGTGGAGAT | TCGATACGTG | 2280 |
| GACTACGGCG | GATATAAGAG | GGTGAAAGTA | GACGTGCTCC | GGCAAATCAG | GTCTGACTTT | 2340 |
| GTCACCCTGC | CGTTTCAGGG | AGCAGAAGTC | CTTCTGGACA | GTGTGATGCC | CCTGTCAGAC | 2400 |
| GATGACCAGT | TTTCACCGGA | AGCAGATGCC | GCCATGAGCG | AGATGACGGG | GAATACAGCA | 2460 |
| CTGCTTGCTC | AGGTGACAAG | TTACAGTCCA | ACTGGTCTTC | CTCTGATTCA | GCTGTGGAGT | 2520 |
| GTGGTTGGAG | ATGAAGTGGT | GTTGATAAAC | CGGTCCCTGG | TGGAGCGAGG | CCTTGCCCAG | 2580 |
| TGGGTAGACA | GCTACTACAC | AAGCCTTTGA | CCCCCATGCT | GCTTCCTGAG | AGTCTTTTTT | 2640 |
| GCACTGTTGA | AATTGGGCTT | GGCACTCAAG | TCAAAGATGA | ACATCGGAAT | AACAAACATT | 2700 |
| GTCCTCTCCA | GAAAGTCCTT | TCTTTATCCA | TACTGTAGTC | CTATTGAGAA | GACATTTCGT | 2760 |
| CTCTGAGAAA | AAAGGATGGA | ACTATGGGTT | CTCTTCGCAA | AGCCAAAGGA | TAGTGTTTAA | 2820 |
| CAAGCCAGCT | GGCTTATCCT | GGCTCGTGCC | | | | 2850 |

ISOLATED POLYNUCLEOTIDES ENCODING PKA-BINDING PROTEINS AND METHODS OF PRODUCING THE PROTEINS RECOMBINANTLY

FIELD OF THE INVENTION

The present invention relates generally to proteins that bind protein kinase A. More specifically, the present invention relates to novel proteins and nucleotide sequences encoding those proteins which localize protein kinase A within cells.

BACKGROUND OF THE INVENTION

Extracellular signals such as hormones and cytokines modulate many cellular processes by activating adenylate cyclase, increasing intracellular levels of cAMP and ultimately activating the cAMP-dependent kinase (PKA). PKA is a ubiquitous enzyme that functions in many intracellular pathways, for example, regulation of glycogen metabolism by reversible phosphorylation of glycogen phosphorylase [Walsh et al., *J. Biol. Chem.*, 243:3763–3765 (1969)], and regulation of MAP kinase signaling by inhibiting Raf-1 activation by Ras [Vojtek et al., Cell, 74:205–214 (1993) and Hafner et al., *Mol. Cell Biol.*, 14:6696–6703 (1994)]. Inactive PKA exists as a tetramer in which two identical catalytic subunits are bound to a dimer of two regulatory subunits. Activation of PKA by cAMP is effected by binding of a cAMP molecule to each of the regulatory subunits (R) causing release of the active catalytic subunit (C). While only one form of the C subunit has been identified, two classes of R subunit exist, RI and RII, with apparently distinct subcellular distributions. The RI isoforms (RIα and RIβ) are reported to be predominantly cytoplasmic and are excluded from the nucleus, whereas up to 75% of the RII isoforms (RIIα or RIIβ) are particulate and associated with either the plasma membrane, cytoskeletal components, secretory granules, golgi apparatuses, centrosomes or possibly nuclei [Scott, *Pharmac. Ther.*, 50:123–145 (1991)]. Presumably, differences (either physical or physiological) in the various R subunits provide a means by which cells are able to restrict activity of the C subunit to a desired pathway.

Recent evidence indicates that cells are able to target PKA activity by localizing the inactive enzyme in the vicinity of potential substrates, thereby restricting the activity of the C subunit following release by cAMP binding to the R subunit. This "compartmentalization" segregates PKA with participants in a given signaling pathway and contributes to PKA specificity in response to different extracellular stimuli. Compartmentalization of PKA occurs, at least in part, by interaction or tethering, of the R subunit with specific proteins which localize, or anchor, the inactive holoenzyme at specific intracellular sites. Proteins which specifically segregate PKA have been designated A Kinase Anchor Proteins, or AKAPs [Hirsch et al., *J. Biol. Chem.*, 267:2131–2134 (1992)]. In view of the fact that some AKAP have been shown to bind, and anchor, other proteins in addition to PKA, the family of proteins is generally referred to as anchoring proteins.

To date, a number of anchoring proteins have been identified [discussed below] which apparently bind PKA by a common carboxy terminal secondary structure motif that includes an amphipathic helix region [Scott and McCartney, *Mol. Endo.*, 8:5–11 (1994)]. Binding of PKA to most, if not all, identified anchoring proteins can be blocked in the presence of a peptide (Ht31) that mimics this common secondary helical structure, while a mutant Ht31 peptide, containing a single amino acid substitution that disrupts the helical nature of the peptide, has no effect on PKA/anchoring protein binding [Carr et al., *J. Biol. Chem.*, 266:14188–14192 (1991)]. Even though PKA/anchoring protein interaction is effected by a common secondary structure, anchoring proteins (or homologous anchoring proteins found in different species) generally have unique primary structure as evidenced by the growing number of anchoring proteins that have been identified in a variety of organisms. Presumably, the unique amino acid structure, most notable in amino terminal regions of the proteins, accounts in part for anchoring proteins identified as unique to various specific cell types and for the various specific intracellular compartments in which PKA localization has been observed.

For example, anchoring proteins which are predominantly expressed in mammalian brain have been identified in the rat (AKAP 150) and cow (AKAP 75) [Bergman, et al., *J.Biol. Chem.* 266:7207–7213 (1991)], as well as in humans (AKAP 79) [Carr, et al., *J.Bio. Chem.* 267:16816–16823 (1992)]. Amino acid identity and immunological cross-reactivity between these neuronal-specific proteins suggest that they represent interspecies homologs. As another example, AKAP 100 appears to be specific for human and rat cardiac and skeletal muscle, while being expressed to a lower degree in brain cells of these mammals. As still another example, AKAP Ht31 [Carr et al., *J. Biol Chem.*, 267:13376–13382 (1992)] appears to be specific for thyroid cells. Conversely, AKAP 95 has been shown to be expressed in a multitude of cell types, showing no apparent tissue or cell-type specificity.

With regard to localization in specific intracellular compartments, AKAP 75, microtubule-associated protein (MAP-2) [Threurkauf and Vallee, *J. Biol. Chem.*, 257:3284–3290 (1982) and DeCamilli et al., *J. Cell Biol.*, 103:189–203 (1986)], AKAP 79 [Glantz et al., *J. Biol. Chem.*, 268:12796–12804 (1993)] and AKAP 150 [Glantz et al., *Mol. Biol. Cell*, 3: 1215–1228 (1992)] are closely associated with cytoskeletal structural proteins, with AKAP 75 more specifically associated with post synaptic densities [Carr et al., J. Biol. Chem., 267:16816–16823 (1992)]. Still other anchoring proteins have been shown to localize with less widespread cellular structures, including AKAP 350 association with centrosomes [Keryer et al., *Exp. Cell Res.*, 204:230–240 (1993)], AKAP 100 with the sarcoplasmic reticulum in rat cardiac tissue [McCartney, et al., *J. Biol. Chem.* 270:9327–9333 (1995)], and an 85 kDa AKAP which links PKA to the Golgi apparatus [Rios et al., *EMBO J.*, 11:1723–1731 (1992)].

AKAP 95, with an apparent zinc finger DNA-binding region, appears to reside exclusively in the nucleus [Coghlan et al., *J. Biol. Chem.*, 269:7658–7665 (1994)]. The DNA binding domain of AKAP 95 provides a role for direct involvement of PKA in gene transcription, possible by positioning of PKA for phosphorylation of transcription factors. Other diverse cellular activities shown to be influenced by anchoring protein/PKA binding have been demonstrated by disruption of the interaction, for example, disruption of PKA/anchoring protein binding in T cells has been shown to reverse cAMP-induced suppression of interleukin 2 expression [Lockerbie et al., *J. Cell Biochem.*, Suppl. 21A:76, Abstract D2155 (1995)] and disruption of PKA/anchoring protein binding in hippocampal neurons has been shown to attenuate whole cell currents through alpha-amino-3-hydroxy-5-methyl-4- isoxazole propionic acid/kainate glutamate receptors [Rosenmund et al., supra.]. The ability of anchoring proteins to regulate IL-2 expression and to regulate glutamate receptor activity, in combination with a previous demonstration that anchoring proteins can bind calcineurin, suggest multiple therapeutic applications for anchoring proteins and molecules which modulate anchoring protein binding to cellular components.

In view of the diversity, both in terms of cell type expression, subcellular localization and physiological activities of anchoring proteins identified to date, there thus exists a need in the art to continue to identify novel anchoring proteins and nucleic acids which encode them. The uniqueness of anchoring protein primary structures provides a target for specifically regulating PKA localization, and thereby its function in specific cellular processes.

SUMMARY OF THE INVENTION

The present invention provides purified and isolated polynucleotide sequences that encode proteins having the biological properties of PKA binding and subcellular compartmentalization. A presently preferred polynucleotide is set forth in SEQ ID NO: 5. Polynucleotides of the invention also encompass polynucleotides that hybridize under stringent hybridization conditions to the polynucleotide of SEQ ID NO: 5. Polynucleotides of the invention may be DNA or RNA and may hybridize to the sense strand or antisense strand of the DNA molecule. The DNA may be cDNA, genomic DNA or chemically synthesized DNA. Polynucleotides of the present invention may be identified by standard techniques such as complementation, low stringency hybridization, and PCR utilizing primers generated based on knowledge of the sequences of polynucleotides of the invention.

Also provided by the present invention are recombinant expression constructs that contain polynucleotides of the invention operably linked to transcriptional regulatory elements such as promoters and transcriptional terminators. The transcriptional regulatory elements may be homologous or heterologous.

Another aspect of the present invention is host cells transformed or transfected with polynucleotides of the invention. The host cells may be procaryotic or eukaryotic. Host cells so transformed or transfected are particularly useful for expression of PKA-binding polypeptides of the present invention, which may be isolated from the cells or the media of their growth.

Yet another aspect of the present invention are PKA-binding polypeptides encoded by the polynucleotides of the present invention. A preferred PKA-binding polypeptide is encoded by the polynucleotide set forth in SEQ ID NO: 5. Polypeptides of the invention may be purified from natural sources or produced by recombinant methods employing the host cells of the present invention. Variant polypeptides which maintain biological activity of a wild-type polypeptide are also contemplated, including analogs wherein additions, deletions or conservative amino acid substitutions have been incorporated which modulate functional or immunological characteristics of the PKA-binding polypeptide. Other variant polypeptides include fusion proteins wherein additional polypeptide sequences are incorporated which facilitate purification or immobilization on assay supports. Additional polypeptides of the present invention may be identified by immunological cross-reactivity with the polypeptide encoded by the polynucleotide of SEQ ID NO: 5.

The present invention also provides polypeptides and non-peptide molecules that specifically bind to the PKA-binding polypeptides described above. Preferred binding molecules include antibodies (e.g., polyclonal, monoclonal, recombinant antibodies or binding fragments thereof). Binding molecules are useful for purification of the PKA-binding polypeptides, identification of cells that express the PKA-binding proteins and modulation of the in vivo interaction between PKA and the PKA-binding polypeptides. Hybridoma cell lines that produce antibodies specifically immunoreactive with the PKA-binding polypeptides of the present invention are also provided. Such hybridomas may be produced and identified by techniques that are well known in the art.

Assays to identify molecules that disrupt the interaction between PKA and the PKA-binding proteins of the present invention are also provided (e.g., immobilized binding assays, solution binding assays, scintillation proximity assays, di-hybrid screening assays, and the like). In some instances, it may be desirable to modulate binding between PKA and the polypeptides of the present invention. In other instances, it may be desirable to specifically modulate the binding between a PKA-binding polypeptide and a cellular component (other than PKA) to which it binds. In either case, the polypeptides of the present invention provide a useful screening target for the assays of the present invention. Assays of the invention may be performed in a variety of formats, including cell-based assays, such as di-hybrid screening or complementation assays as described in U.S. Pat. No. 5,283,173 and Patent Cooperation Treaty (PCT) Publication No. WO 91/16457, respectively. Assays of this type are particularly useful for assessing intracellular efficacy of compounds. Non-cell-based assays of the invention include scintillation proximity assays, cAMP competition assays, ELISA assays, radioimmunoassays, chemiluminescent assays, and the like. Such assay procedures are well known in the art and generally described, e.g., in Boudet et al., *J. Immunol. Meth.*, 142:73–82 (1991); Ngai et al., *J. Immunol. Meth.*, 158:267–276 (1993); Pruslin et al., *J. Immunol. Meth.*, 137:27–35 (1991); Udenfriend et al., *Proc. Natl. Acad. Sci. USA*, 82:8672–8676 (1985); Udenfriend et al., *Anal. Biochem.*, 161:494–500 (1987); Bosworth and Towers, *Nature*, 341:167–168 (1989); Gilman, *Proc. Natl. Acad. Sci. USA*, 67:305–312 (1970);; and U.S. Pat. No. 4,568,649. The utility of compounds which modulate anchoring protein binding is manifest. For example, small molecules may be found to inhibit either PKA/anchoring protein binding or anchoring protein interaction with specific cellular components. Modulators of this type would delocalize specific pools of PKA and affect only a targeted signaling pathway. Identification of modulators of anchoring protein binding to other cellular components may be equally beneficial. For example, factors which affect calcineurin activity in a manner similar to previously identified immunosuppressants, but have fewer side effects may be useful in treatment of conditions now treated with more the toxic immunosuppressants. In addition, identification of factors which modulate anchoring protein participation in cellular activities may also be useful in replacing currently accepted therapeutic intervention. For example, factors which regulate anchoring protein regulation of IL-2 expression may be useful in replacing administration of exogenous, recombinant IL-2.

DETAILED DESCRIPTION OF THE INVENTION

The following examples are offered by way of illustration and not of limitation. Example 1 addresses identification of a T cell-specific anchoring protein proteins from a human cDNA library. Example 2 describes RII binding specificity of the identified anchoring protein. Example 3 relates determination of the anchoring protein nucleotide sequence. Example 4 addresses expression of the anchoring protein clone. Example 5 relates to cellular and tissue distribution of the anchoring protein. Example 6 describes potential therapeutic applications of the anchoring protein and molecules which modulate anchoring protein binding.

EXAMPLE 1

Identification of T Cell-Expressed Anchoring Proteins

In an attempt to identify novel T cell anchoring proteins, a human Jurkat T cell cDNA library subcloned into ZAPII Express (Stratagene, La Jolla, Calif.) was screened by RIIα overlay techniques as described in Carr et al., *J. Biol. Chem.*, 267:16816–16823 (1992).

Briefly, one µl of the library phage ($5 \times 10^4$ pfu) was added to 600 µl *E.coli* strain XL-1 Blue MRF' (Stratagene) in 10 mM $MgSO_4$ grown to $OD_{600} = 0.5$. The bacteria and phage were incubated at 37° C. for 15 minutes, after which time 7.5 ml top agar (NZY media (1% [w/v] N-Z-Amine Type A, 0.5% [w/v] yeast extract, 86 mM NaCl, 8 mM $MgSO_4 7H_2O$, 1.5% [w/v] Bacto agar, pH 7.5), 0.7% agarose) was added to the suspension. The resulting mixture was immediately plated onto NZY plates prewarmed to 37° C. The plates were allowed to cool to room temperature and incubated at 42° C. for 4 hours. Nitrocellulose filters, presoaked in 10 mM isopropyl-1-thio-β-D-galactopyranoside (IPTG), were placed on the plates and the plates further incubated for 4 hours at 37° C. The filters were removed and washed 3 times in TBS (50 mM Tris, pH 7.5, 150 mM NaCl), and blocked overnight at 4° C. in Block (TBS, 5% non-fat milk, 0.1% BSA). A second set of similarly prepared nitrocellulose filters was overlaid on the plates and incubated at 4° C overnight. The filters were washed (as described above) and blocked (also as described above) for one hour at room temperature.

Approximately 4 µjg (6 µl) recombinant mouse RIIα were mixed with 2.35 µg (0.5 µl) recombinant bovine catalytic subunit of PKA in a reaction containing 2.5 µl [$^{32}$P]ATP (25 µCi, 3000 Ci/mmole), and 1 µl buffer (containing 0.5 M MOPS, pH 7.0, 0.5 M NaCl, 20 mM $MgCl_2$, and 10 mM DTT). The reaction was allowed to proceed for thirty minutes at 30° C., after which unincorporated label was removed using an Execellulose GF-5 column (Pierce). Filters were probed with [$^{32}$P]RIIα(100,000 cpm/ml in Block) for 6 hours at room temperature. After incubation, the filters were washed 3 times in TBS containing 1 % Tween-20 and exposed to x-ray film for 16 hours.

Of the approximately $1 \times 10^6$ plaques screened, one positive plaque, Plaque #11, was identified as binding labeled RIIα. A secondary screen was carried out on Plaque #11, by the techniques described in the initial screen, which indicated that progeny of Plaque #11 were also capable of binding radiolabeled RIIα.

EXAMPLE 2

Specificity of RIIα Binding to Plaque #11

In view of previous reports that peptide Ht31 (SEQ ID NO: 1) is generically capable of blocking PKA binding to anchoring proteins and that a proline mutant of Ht31 (see SEQ ID NO: 2 below wherein the proline substitution is indicated in bold and underlined), also described above, is not, specificity of RIIα binding to Plaque #11 was determined in parallel experiments in which RIIα overlays were performed in the presence of either Ht31peptide.

Asp—Leu—Ile—Glu—Glu—Ala—Ala—Ser—Arg—Ile—Val—

Asp—Ala—Val—Ile—Glu—Gln—Val—Lys—Ala—Ala—Gly—Ala (SEQ ID NO: 1)

Asp—Leu—Ile—Glu—Glu—Ala—Ala—Ser—Arg—Pro—Val—

Asp—Ala—Val—Ile—Glu—Gln—Val—Lys—Ala—Ala—Gly—Ala (SEQ ID NO: 2)

Briefly, nitrocellulose filter lifts were prepared as described in Example 1, except that the resulting plaque lifts were pre-incubated for 15 minutes at room temperature in Block containing 1 µM of either the Ht31 peptide or the proline mutant Ht3 peptide. Following preincubation, filters were probed with [$^{32}$P]RIIα as described in Example 1 and the filters subsequently subjected to autoradiography.

The autoradiograms revealed that pre-incubation of Plaque #11 with the Ht31 peptide blocked binding of [$^{32}$P] RIIα, while pre-incubation with the proline mutated Ht31 peptide had no effect. These results indicate that RIIα binding to the polypeptide encoded by Plaque #11 is effected by a secondary structure of Plaque #11 similar to that utilized by previously identified anchoring proteins.

EXAMPLE 3

Cloning of Plaque #11 cDNA

In an attempt to determine the nucleotide sequence of the insert in the phage of Plaque #11 and to deduce the amino acid sequence of the encoded protein, the cDNA insert of Plaque #11 was excised in vivo using an ExAssist/XLOLR System (Stratagene) according to the manufacturers instructions.

Briefly, Plaque #11 was removed from the NZY plate and mixed with 500 µl of SM buffer (100 mM NaCl, 8 mM $MgSO_4 7H_2O$, 50 mM Tris-HCl pH 7.5, 0.01% [w/v] gelatin) and 20 µl of chloroform. The mixture was vortexed and stored at 4° C. (phage stock). XL-1 Blue MRF' and XLOLR cells (both from Stratagene) were grown separately overnight at 30° C. in LBM medium supplemented with 10 mM $MgSO_4 7H_2O$ containing 0.2% (v/v) maltose. A 1/100 dilution of XL-1 Blue MRF' cells was prepared with 0.5 ml of the overnight culture medium and 50 ml of LBM media and the dilution was grown at 37° C. for 2–3 hours to mid-log phase ($OD_{600} = 0.2$–$0.5$ for XL-1 Blue MRF' cells, or $OD_{600} = 0.5$–$1.0$ for XLOLR cells). The culture was centrifuged at 1500×g and the resulting pellet resuspended in 10 mM $MgSO_4 7H_2$ O to a density of $OD_{600} = 1.0$.

Two hundred µl of the XL-1 cells, 250 µl of the phage stock suspension as described above, and 1 µl of ExAssist helper phage (Stratagene) were combined and incubated for 15 minutes at 37° C. Three ml of LBM media were added and the mixture was further incubated for 2.5 hours at 37° C. with shaking. After incubation, the mixture was centrifuged for 15 minutes at 2000×g. The supernatant was withdrawn, incubated at 70° C. for 15 minutes, and centrifuged at 4000×g for 15 minutes. The resulting supernatant contained filamentous phage which packaged Plaque #11 DNA in phagemid pBK-CMV. The phagemids were rescued by mixing 200 µl of the XLOLR cells (prepared as described above) with 10 µl of the phagemid stock and incubating for 15 minutes at 37° C. Following incubation, 300 µl of LBM media was added and the mixture was further incubated for 45 minutes at 37° C. The resulting cellular suspension was plated at 200 μl/plate on LBM containing 50 μg/ml kanamycin.

Plasmid preparation was carried out by standard procedures and included use of a Wizard Miniprep Kits (Promega). Plasmid DNA isolated from Plaque #11 was designated clone # 11. The cDNA insert was excised from the vector by digestion with EcoRI and BamHI and the resulting fragments separated using agarose gel electrophoresis. The Clone # 11 insert was determined to be 2850 bp in length. Nested deletions of clone # 11 were generated with an Erase-a-Base System (Promega, Madison, WI) and clone # 11 was sequenced using Universal T3 (ATTAACCCTCACTAAAG [SEQ ID NO: 3]) and T7 (GATATCACTCAGCATAA [SEQ ID NO: 4]) primers and a Prism Ready Reaction DyeDeoxy Terminator Cycle Kit (Perkin Elmer) in an ABI373 DNA Sequencer (Perkin Elmer, Foster City, Calif.).

The DNA sequence of clone # 11 is set out in SEQ ID NO: 5. Because no appropriate initiation codon could be detected in the nucleotide sequences, a deduced amino acid sequence and a molecular weight for clone # 11 were not possible to determine. A nucleotide level Blast Search (Jun. 16, 1995, 14:01:37 EDT) of the sequence obtained from the T3 primer showed homology to a clone designated "Homo Sapiens cDNA 3'-end similar to none" (accession # T32770), while sequence data obtained from the T7 primer showed 98% homology over a stretch of 343 bases from 1905-2248 of clone # 11 to a clone designated "Homo Sapiens partial cDNA 5 ' end similar to none"; (accession # T31099). In addition, clone # 11 showed 98% homology over a stretch of 332 bases from nucleotides 2308-2640 to a clone designated "Homo Sapiens partial cDNA sequence, clone 66D04 (accession # Z 24883).

EXAMPLE 4

Expression of Clone # 11

In order to determine an approximate molecular weight for the gene product of clone # 11, an overnight culture of clone # 11 in XLOLR cells (prepared as described in Example 3) was grown in LBM media/tetracycline (12.5 μg/ml) and subsequently used to inoculate 250 ml of the same media. Incubation was allowed to proceed at 37° C. to an $OD_{600}$=1.2, after which the bacteria were pelleted at 6000×g for 15 minutes. The pellet was weighed and resuspended in 10 volumes (w/v) FP buffer (1% Triton X-100, 150 mM NaCl, 1 mM EGTA, 1 mM EDTA, 10 mM Tris, pH 7.4, 1% Aprotinin, 0.2% $NaN_3$). The cells were cracked in a French Press and the lysate clarified by centrifuging at 40,000×g for 30 minutes. The lysate was then concentrated using a Centricon-10 (Amicon). An aliquot of the concentrated lysate was loaded onto a 10% Tris-glycine gel (Novex), electrophoresed and transferred to Immobilon (Millipore). The blot was probed with [$^{32}$P]RIIα. A single band of approximately 120 kD was detected, which was partially competed away by the HT31 peptide. These results indicate that clone # 11 encodes a PKA-binding protein that can be used in assays to identify inhibitors of binding between PKA-binding polypeptides and PKA.

EXAMPLE 5

Cellular and Tissue Distribution of Clone # 11

In order to determine the cellular and tissue distribution of clone # 11 expression, reverse transcriptase PCR (RT-PCR) was utilized to assess clone # 11 mRNA levels.

Briefly, primers were initially designed to span 300 bp of clone # 11 sequence, based on the nucleic acid sequence determined in Example 3. In the sequence for clone # 11 (SEQ ID NO: 5), primer 2T3 corresponds to nucleotides 266-283, primer M2T3 to nucleotides 434-453, primer R2T3 to nucleotides 601-622, primer R2T7 to nucleotides 2229-2250, primer M2T7 to nucleotides 2337-2400, and primer 2bT7 to nucleotides 2256-2592. RNA was prepared from various cell and tissues types (described below in discussion of the results) using an RNA Isolation Kit (Stratagene). RT-PCR was carried out as follows. RNA (approximately 1 μg in 10 μl water) was initially denatured by incubation at 80° C. for three minutes, after which the RNA was further incubated on ice until reverse transcriptase reactions were carried out as follows. Denatured RNA was mixed with 8 μl 5X MMuLV-RT buffer (Boehringer), 8 μl 2.5 mM dNTP mixture, 1 μl water containing 0.5 μg each of 2T3 and R2T3 primers or 2bT7 and R2T7 primers, 1 μl RNAse inhibitor (Boehringer), 1 μl MMuLV-RT (Boehringer) and 11 μl water and incubated for one hour at 42° C.

PCRs were carried out as follows. Two μl from the preceding reverse transcriptase reaction were mixed with 3 μl 2.5 mM dNTP mixture, 3 μl 10X Taq polymerase buffer (Boehringer), 3 μl (0.3 μg) 2T3 primer with 3 μl (0.3 μg) R2T3 primer, or 3 μl (0.3 μg) 2bT7 primer with 3 μl (0.3 μg) R2T7 primer, 0.5 μl Taq polymerase, and 14.5 μl water. The mixture was heated to 94° C. for four minutes, after which thirty reaction cycles (94° C. for one minute, 60° C. for one minute and 72° C. for one minute) were completed.

Amplification products from the PCRs were separated by electrophoresis on 1% agarose gel, and subsequently transferred to Nytran Plus membrane (S+S) by standard procedures. PCR products were crosslinked to the membrane with UV irradiation and the membrane subsequently prehybridized for three hours at 42° C. in 5X SSPE, 0.5% SDS, 0.1 mM Tris, pH 7.5, and 2X Denhardt's.

Hybridization probes were prepared by end labeling as follows. Two μl (200 ng) of primer M2T3 were mixed with 2 μl primer M2T7 (200 ng), 2 μl 10X polynucleotide kinase buffer (Boehringer), 10 $^{32}$P-ATP (100 μCi, 3000 Ci/mmole), 2 μl (20 units) T4 polynucleotide kinase (Boehringer), and 2 μl water. The reaction was allowed to proceed at 37° C. for thirty minutes, after which the reaction was stopped by addition of 2 μl 0.5 M EDTA and unincorporated label was removed by centrifugation with a Centristep column (Princeton Separation, Inc.). The membrane was then probed overnight at 42° C. in the same prehybridization buffer but further containing 400 ng (200 ng each) of $^{32}$P-labeled primers M2T3 and M2T7. After hybridization, membranes were washed at room temperature three times for ten minutes each in 0.5X SSC, with 0.2% SDS, and subsequently autoradiographed.

Cell based results indicated that clone # 11 was expressed Ramos cells (B cell), Jurkat cells T cell), U973 cells (monocyte), T84 cells (colon carcinoma), HL60 cells (promyelocytic leukemia), A549 cells (lung epithelia), and HeLa (epithelial carcinoma). Results from tissue analysis indicated that clone # 11 was expressed in human testes, liver and occipital cortex of the brain.

EXAMPLE 6

Potential Therapeutic Applications

The previous demonstration that AKAP 79 binds calcineurin is relevant in view of the fact that calcineurin is the target of two potent and clinically useful immunosuppressive, cyclosporin and FK506, both of which inhibit calcineurin activity. As described below, both cyclosporin and FK506 are useful in treatment of a variety of diseases, but have significant limiting side effects. Presumably, factors which modulate anchoring protein/calcineurin binding may ultimately modulate calcineurin activity in a manner similar to the activities of cyclosporin or FK506. Identification of such a modulator, particularly with fewer side effects than those observed with other immunosuppressants, would possibly have widespread therapeutic use treatment of a multitude of disease currently treated with cyclosporin or FK506.

Numerous clinical indications of cyclosporin and FK506 have been reported. For example, cyclosporin has defined the standard for post-transplant immunosuppression, making possible liver, lung, intestine, and pancreas transplants, even though FK506 is generally believed to be a stronger immunosuppressive. Transplant patients who do not tolerate or fail on either cyclosporin or FK506 are sometimes successfully changed to the other drug.

As another example, inflammatory bowel disease (IBD) is a common term for two diseases having different clinical appearances, Crohn's disease and ulcerative colitis (UC). Cyclosporin has been successfully used to treat Crohn's disease, with statistically significant results of treatment having been demonstrated in at least one index of disease activity [Brynskov, *Dan.Med.Bull.* 41:332–344 (1994)]. Other indices, however, that correlate best with resolution of acute exacerbations showed non-significant trends toward improvement. Cyclosporin has also shown activity in severe acute steroid-resistant UC (the data are not significant as the trial was stopped for ethical reasons). Another trial of patients with sclerosing cholangitis and UC demonstrated borderline significance toward a milder course of UC. Relapse was common after withdrawal and treatment has been limited by concern for toxicity [Choi and Targan, *Dig.Dis. and Sci.* 39:1885–1892 (1994)]. In addition, other immunosuppressives have been used successfully in IBD, such as methotrexate, azathioprine, and 6-MP.

As another example, cyclosporin has been demonstrated to be effective in treating rheumatoid arthritis in several trials when used as a second or third line therapy of the disease, i.e., in patients that have failed other established therapies and have severe disease. In these trails, cyclosporin was found to be generally as effective and toxic as other second-line agents, such as gold, antimalarials, azathioprine, D-penicillamine, and methotrexate [Wells and Tugwell, *Br.J.Rheum.*, 32(suppl 1):51–56 (1993); Forre et al., *Arth.Rheum.*, 30:88–92 (1987)]. The trials only report treatment of "very severe, refractory active RA" because of cyclosporin's "potentially irreversible toxicity" [Dougados and Torley, *Br.J.Rheum.*, 32(suppl 1):57–59 (1993)]. The renal toxicity is thought to have been primarily mediated through renal vasoconstriction that exacerbates NSAID nephrotoxicity and renal disease inherent in rheumatoid arthritis [Leaker and Cairns, *Br. J.Hosp.Med.*, 52:520–534 (1994); Sturrocketal., *Nephrol.DiaL Transplant*, 9:1149–1156 (1994); Ludwin and Alexopolulou, *Br.J.Rheum.*, 32(suppl1):60–64 (1993)]. About 10% of renal biopsies from RA patients treated with cyclosporin showed morphological features of cyclosporin toxicity [International Kidney Biopsy Registry of Cyclosporin in Autoimmune Diseases, *Br.J.Rheum.*, 32(suppl 1):65–71 (1993)].

As still another example, cyclosporin has been reported to be effective for treatment of steroid-dependent asthma. In one trial, a small number of patients were randomized to cyclosporin or placebo, and the cyclosporin group exhibited increased airflow and FVC as well as fewer rescue courses of prednisolone.

As another example, cyclosporin was shown to be effective in the treatment of steroid-dependent minimal change disease nephrotic syndrome. Patients in this trail were shown to have lower steroid requirements on low dose cyclosporin, but all relapsed when cyclosporin was discontinued. Steroid-resistant forms of nephrotic syndrome have only a 20–30% response rate to cyclosporin [Meyrier, *Nephrol. Dial. Transplant*, 9:596–598 (1994); Hulton et al., *Pediatr.Nephrol.*, 8:401–403 (1994)].

With regard to treatment of systemic lupus erythematosus (SLE), one study reported significant decrease of SLE activity indices in a prospective non-randomized, non-controlled study [Tokuda et al., *Arthr.Rheumat.*, 37:551–558 (1994)]. Other studies, however, have not demonstrated efficacy in SLE.

As another example, cyclosporin has been shown to induce remission in insulin-dependent diabetes mellitus when instituted early after initial presentation. Remissions averaged about one year, although some were extended up to 850 days [Jenner et al., *Diabetologia*, 35:884–888 (1992); Bougneres et al., *Diabetes*, 39:1264–1272 (1990)]. No long-lasting effect of cyclosporin was noted in extended follow-up of one study [Martin et al., *Diabetologia*, 34:429–434 (1991)]. In another study, however, renal function deteriorated during treatment for 12–18 months and did not return completely to placebo level indicating that some chronic renal injury may have occurred [Feldt-Rasmussen et al., *Diabetes Medicine*, 7:429–433 (1990)]. Earlier intervention would be needed to enhance the effect of immunosuppressive therapy on the course of insulin-dependent diabetes mellitus. Some investigators are screening first degree relatives and successfully prophylactically treating those with diabetic markers [Elliott and Chase, *Diabetologia*, 34:362–365 (1991)].

As still another example, psoriasis has been effectively treated by cyclosporin [Cuellar et al., *Balliere's Clin.Rheum.*, 8:483–498 (1994); Ellis et al., *JAMA* 256:3110–3116 (1986)]. High dose therapy was effective for treatment of psoriatic arthritis, a particularly serve form of destructive arthritis, and discontinuation of therapy was generally followed by exacerbation of skin and joint disease. In view of the potential side effects and the need for continuous long term treatment, cyclosporin is only indicated for refractory psoriatic arthritis that is not adequately treated by other means.

In addition, cyclosporin has been demonstrated to be effective for treatment of severe atopic dermatitis in placebo-controlled and double-blinded studies [Van Joost et al., *Br.J.Derm.*, 130:634–640 (1994); Cooper, *J.Invest.Denn.*, 102:128–137 (1994)]. Side effects of nausea, abdominal discomfort, paresthesias, cholestasis, and renal insufficiency from the drug were preferred by patients to their untreated disease. Another randomized double-blind, placebo-controlled study found that cyclosporin treatment significantly increased the quality of life for patients with severe atopic dermatitis [Salek et al., *Br.J.Dern.*, 129:422–430 (1993)]. Skin lesions quickly relapsed following cessation of cyclosporin, but quality of life remained improved.

As still another example, cyclosporin has been used in treatment of chronic dermatitis of the hands, a disease with a reported prevalence of 4–22%, and typically treated with topical steroids to which many patients, however, do not respond. Low dose cyclosporin has been shown to effectively treated 6/7 patients in an open study [Reitamo and Granlund, Br.J.Derm., 130:75–78 (1994)]. Approximately half of the patients relapsed after cyclosporin was discontinued.

As still another example, cyclosporin has been utilized in treatment of urticaria and angioedema, idiopathic skin diseases that present as hives and subcutaneous swelling. The pathology is related to mast cells, and treatment is often ineffective. IN one trail, three patients with refractory urticaria and angioedema were treated with cyclosporin and all symptoms resolved within one week [Fradin et al., J.Am.Acad.Denn., 25:1065–1067 (1991)]. All patients had to stop therapy because of side effects, and symptoms recurred after therapy was discontinued.

With regard to other rheumatological diseases, studies report effective cyclosporin treatment of other less common autoimmune diseases, including Behcet's Disease [Pacor et al., Clin.Rheum., 13:224–227 (1994)], Wegner's Granulomatosis [Allen et al., Cyclospornin A Therapy for Wegner's Granulomatosis in ANCA-Associated Vasculidites: Immunological and Clinical Aspects, Gross ed. Plenum Press (1993)], and immune-mediated thrombocytopenia [Schultz et al., Blood 85:1406–1408 (1995)].

In many of the trials described above, use of cyclosporin or FK506 was associated with many undesired side effects. In general, increased risk of infection and malignancy are associated with general immunosuppression, and it is unlikely that an anchoring protein-related immunosuppressive would not have similar risks. Other side effects may be avoided or reduced, however, by anchoring protein tissue specificity. The most common serious side effect of both cyclosporin and FK506 is nephrotoxicity, which at least to some degree is dose related and occurs in most patients, generally in the form of a decrease in the glomerular filtration rate during treatment. This side effect, however, is at least partially reversible when the drug is discontinued [Leaker and Cairns, supra]. Typically, progressive renal insufficiency does not develop, although more follow-up is needed for definitive evaluation. Chronic injury has also been observed in patients receiving low dose cyclosporin (3–4 mg/kg/d), about 40% of biopsies of these patients showed changes of interstitial fibrosis, tubular atrophy, and arteriolopathy [Svarstad et al., Nephrol.Dial. Transplant, 9:1462–1467 (1994); Young et al., Kidney International, 46:1216–1222 (1994)]. Changes in endothelial cells were also apparent in histological sections [Kahan, N.Engl.J.Med., 321:1725–1748 (1989)]. The nephrotoxicity was postulated to have resulted primarily due to arteriolar vasoconstriction and chronic low-grade ischemia [Leaker and Carins, supra], although the drugs were also shown to be directly toxic to tubular cells and vascular interstitial cells [Platz et al., Transplantation, 58:170–178 (1994)]. Some reports indicate that the incidence and severity of nephrotoxicity may be slightly higher with FKSO6 [Platz et al., supra].

Another reported significant toxicity of both cyclosporin and FK506 was neurotoxicity, with clinical manifestations including seizures, confusion, blindness, coma, headache, ataxia, Parkinson's syndrome, paresthesias, psychosis, focal deficits, akinetic mutism, tremors, neuropathy, and sleep disturbances [Shimizu et al., Pediatr. Nephrol., 8:483–385 (1994); Wilson et al., Muscle and Nerve, 17:528–532 (1994); Reece et al., Bone Marrow Transpl., 8:393–401 (1991); Eidelman et al., Transpl.Proc., 23:3175–3178 (1991); de Groen et al., N.Engl.J.Med., 317:861–566 (1987)]. Following liver transplantation, moderate to severe neurotoxicity has been shown to occur in 10–20% of patients treated with FK506 and 3–12% of patients treated with cyclosporin. Neurotoxicity has also been associated with serum lipid abnormalities and liver dysfunction.

Other side effects of cyclosporin and/or FK506 include hepatotoxicity, glucose intolerance, hypertension, hirsutism, gastrointestinal symptoms, venous thrombosis, pancreatitis, and gingival hyperplasia [Morris, J.Heart Lung Transplant, 12:S275–S286 (1993); Fung et al., Transpl. Proc., 23:3105–3108 (1991); Mason, Pharmacol. Rev., 42:423–434 (1989); Kahan, N.Engl.J.Med., 321:1725–1738 (1989); Thomason et al., Renal Failure, 16:731–745 (1994)]. Therefore, in view of the widespread utilization of cyclosporin and FK506 and the inherent side effects of their use, development of alternative immunosuppressives could be extremely beneficial.

For example, it is possible that delocalization of calcineurin from a putative T cell anchoring protein might inhibit calcineurin activity in T cell activation, and thereby providing a T cell-specific immunosuppressive having the utility of cyclosporin or FK506, but fewer side effects. The previous observation that delocalization of PKA from a T cell anchoring protein enhanced IL-2 expression in stimulated cells indicated that anchoring protein-localized PKA in some way contributes to a regulatory role in IL-2 expression during T cell activation. T cell-specific delocalization of PKA may therefore provide a means for enhancing IL-2 secretion in vivo, thereby mimicking recombinant IL-2 administration and possibly reducing previously reported toxicity of IL-2 treatment as described below.

IL-2 has been approved for treatment of metastatic renal carcinoma and approximately 15–20% of patients with metastatic renal cell carcinoma or malignant melanoma respond to IL-2 therapy. Some of these responses are durable, lasting more than 66 months [Dillman, Cancer Biotherapy, 9:183–209 (1994); Whittington and Faulds, Drugs 46:446–514 (1993)]. While high dose bolus therapy has been associated with several severe side effects (as described below), low dose subcutaneous or continuous infusion therapy produced a modest response rate (12%) while reducing toxicity [Vogelzang et al., J. Clin. Oncol., 11: 1809–1816 (1993)].

IL-2 therapy (with and without interferon-αand other agents) has been investigated in the treatment of other malignancies. For example, sustained clinical responses, but no cures, have been obtained in direct application of IL-2 to tumor beds following glioma resection [Merchant et al., J.Neuro., 8:173–188 (1990)]. In still other trails, limited efficacy has been reported in lymphoma [Dillman, supra], colorectal carcinoma [Whittington and Faulds, supra], limited AML [Bruton and Koeller, Pharmacotherapy, 14:635–656 (1994)], ovarian cancer and early bladder cancer [Whittington and Faulds, supra.]. The number of participants in each of these studies was too small to permit significant conclusions regarding effectiveness, however.

IL-2 has also been used in combination with adoptive immunotherapy, and been demonstrated to be effective for treatment of metastatic renal carcinoma [Pierce et al., Sem. Oncol., 22:74–80 (1995); Belldegrun et al., J. Urol., 150:1384–1390 (1993)]. In addition, IL-2 may also be effective for treatment of certain infectious diseases, by decreasing skin bacterial load and levels of antigen in patients with leprosy following by intradermal injection [Kaplan, J.Infect.Dis., 167(suppl 1):S18–22 (1993)]. Also it has been observed that, as compared to PPD-positive healthy controls, lymphocytes from patients with tuberculosis produce lower levels of IL-2 [Sanchez et al., *Inf.Immun.*, 62:5673-5678 (1994)], suggesting that IL-2 therapy may be of value in treatment of mycobacterial infections.

Despite the potential therapeutic value of IL-2, the cytokine is also associated with significant toxicity [unless otherwise noted, sources are Whittington and Faulds, Dillman and Bruton and Koeller, supra]. The major treatment-limiting side effects is capillary leak syndrome. IL-2 administration increases vascular permeability causing interstitial and pulmonary edema, with patients developing hypotension with a substantial number requiring pressors. Vigorous fluid resuscitation can cause life-threatening pulmonary edema. Up to 20% of patients may require intubation and mechanical ventilation. High does bolus administration causes more severe leak than low dose or slow continuous infusions, and in some regiments, 100% of patients require ICU support during IL-2 treatment. Myocarditis, cardiomyopathies and cardiac arrhythmias have also been observed. Acute renal failure may occur as a result of the capillary leak syndrome-induced sypotension.

IL-2 can also cause severe diarrhea with electrolyte imbalances, cholestasis, thyroid abnormalities, and acute pancreatitis. Anemia requiring transfusions occurs in 15-20% of treated patients [MacFarlane et al., *Cancer* 75:1030-1037 (1995)]. Thrombocytopenia with hemorrhage can occur and coagulation pathway defects are common. Over 70% of patients experience changes in mental status, including paranoid delusions, hallucinations, loss of interest, sleep disturbances, and drowsiness. Coma, visual defects, transient ischemic attacks, and paresthesias have also been reported. These drawbacks associated with exogenous with exogenous IL-2 suggest that alternatives, wherein, for example, endogenous IL-2 production can be modulated and thus eliminate the requirement for exogenous IL-2 treatment, should be explored as potential therapeutics.

In addition to providing possible means to identify immunosuppressive drugs and modulators of IL-2 production, identification of anchoring proteins makes regulation of other cellular activity possible in view of the diverse metabolic pathways in which anchoring proteins have been shown to participate. For example, AKAP 79 is important in regulation of glutamate receptor-regulated ion channels in the post-synaptic density of neurons, presumably via binding PKA, PKC, and calcineurin. PKA regulates activity of AMPA receptor-regulated channels, and delocalization or inhibition of PKA attenuates AMPA ion channel activity. PKC regulates activity of NMDA receptor-regulated channels, and calcineurin has been shown to desensitize the NMDA receptor to stimuli. These observations indicate that localized kinases (PKA and PKC) may regulate activity of glutamate receptors in neurons. Dephosphorylation by calcineurin is the counter-regulatory mechanism of the NMDA receptors. This model agrees physiologically with evidence of seizures induced by cyclosporin or FK506.

In addition, glutamate receptors have been implicated in many neurological diseases. Glutamate and other excitatory amino acids can produce excitotoxicity in neurons, and excessive stimulation of postsynaptic glutamate receptors has been shown to be toxic to the neurons, causing acute neuronal degeneration. Hypoxia (such as following stroke or cardiac arrest) and CNS trauma have been shown to cause a marked outpouring of glutamate into the extracellular space, which then interacts with glutamate receptors and triggers the excitotoxic cascade. Anti-excitatory agents have been shown to protect against brain injury in animals models [Olney, *Neurobiology of Aging*, 15:259-260 (1994)]. Interestingly, NMDA antagonists are toxic to some types of neurons indicating that glutamate may inhibit other excitatory pathways in those cells. Macrolide antibodies, such as FK506, have also been shown to protect against NMDA, but not kainate, excitotoxicity in cultured neurons [Manev, et al., *Brain Res.*, 624:331-335 (1993)].

Glutamate has also been implicated in Parkinson's Disease. NMDA antagonists protect dopaminergic neurons in substantia nigra in monkeys exposed to MPTP, a chemical that induces Parkinson's syndrome in humans and other primates. Amantadine and memantine are NMDA antagonists and have been used in Europe to treat Parkinson's disease, however, both have been shown to cause psychosis in some patients. There is also some evidence that glutamatergic neurons may be hyperactive in Parkinson's disease and inhibition could decrease the motor symptom's of the disease [Lange and Riederer, *Life Sciences*, 55:2067-2075 (1994)].

Glutamate also plays a role in seizure disorders, participating in initiation, spread, and maintenance of seizure activity. NMDA and non-NMDA antagonists are potent anticonvulsants [Meldrum, *Neurology*, 44(suppl 8):S14-S23 (1994)]. AMPA receptors have also been implicated in ALS and a trial of a receptor antagonist is currently in progress.[49]

In view of the total of these observations, it is not surprising that numerous other immunosuppressants are in clinical trials. The following information regarding such trails was obtained from Haydon and Haynes, *Balliere's Clin. Gastroentero.*, 8:455-464 (1994); Thomason and Starzi, *Immunol.Rev.* 1993, 71-98 (1993); and Morris *J.Heart Lung Transplant.*, 12:S275-S286 (1993). For example, azaspirane is an SKB compound that suppresses graft cellular infiltrates and induction of IL-2R, and also abolishes IL-2 and IFN-γ production. Apparently azaspirane induces some type of suppressor cell and there is some evidence of synergistic effects with cyclosporin.

As another example, mycophenolate mofetial is a Syntex compound which inhibits purine synthesis and has a T and B cell-selective antiproliferative effect. It depletes antibodies. Mycophenolate mofetial may also deplete adhesion molecules from cell surfaces. While the drug apparently has low toxicity, it may cause leukopenia, and has been used to treat psoriasis for 20 years.

As another example, mizoribine in a Sumitomo compound which inhibits DNA synthesis. The mechanism of action is identical to mycophenolate.

As another example, brequinar is a DuPont-Merck compound which inhibits pyrimidine synthesis by blocking dihydoorate dehydrogenase. Full reports of clinical trials are awaited. The drug has been reported to act synergistically with cyclosporin, but can cause thrombocytopenia, dermatitis and mucositis.

As still another example, 15-Deoxyspergualin is a Nippon-Kayaku compound which predominantly affects monocyte/macrophage function, including inhibition of oxidative metabolism, lysosomal enzyme synthesis, IL-1 production, and cell surface expression of MHC class II antigens. It is 70–90% effective in refractory kidney rejection, but bone marrow toxicity may occur at higher doses.

As another example, leflunomide is a Hoechst compound which inhibits cytokine action, blocks T cell activation and antibody synthesis. It is not toxic to the kidneys or bone marrow.

As another example, rapamycin is a Wyeth-Ayerst compound that is related to FK506. It is a prodrug that must bind an immunophillin to be active and does no inhibit calcineurin or block T cell cytokine production. By an unknown mechanism, rapamycin blocks Gl to S transition.

Numerous modifications and variations in the invention as set forth in the above illustrative examples are expected to occur to those skilled in the art. Consequently only such limitations as appear in the appended claims should be placed on the invention.

What is claimed is:

1. A purified and isolated polynucleotide encoding an A Kinase Anchor Protein (AKAP) polypeptide having the biological activity of Protein Kinase A (PKA) binding and PKA subcellular localization; said polynucleotide comprising the protein coding sequence set out in SEQ ID NO: 5.

2. The polynucleotide of claim 1 which is a DNA molecule.

3. The DNA molecule of claim 2 which is a cDNA molecule.

4. The DNA molecule of claim 2 which is a genomic DNA molecule.

5. The DNA molecule of claim 2 which is a wholly or partially chemically synthesized DNA molecule.

6. A DNA expression construct comprising a DNA molecule according to claim 2.

7. A host cell transformed with a DNA molecule according to claim 2.

8. A method for producing a human polypeptide encoded by the polynucleotide set out in SEQ ID NO: 5 comprising growing a host cell according to claim 7 in a suitable medium and isolating the polypeptide from said host cell or the medium of its growth.

9. A purified and isolated polynucleotide encoding the A Kinase Anchor Protein (AKAP) polypeptide encoded by the polynucleotide of SEQ ID NO: 5.

10. A purified and isolated polynucleotide encoding an A Kinase Anchor Protein (AKAP) polypeptide having the biological activity of Protein Kinase A (PKA) binding and PKA subcellular localization; said DNA hybridizing to the non-coding strand of the DNA of SEQ ID NO: 5 under stringency conditions of 2.5 mM $MgCl_2$, 10 mM Tris-HCl, and 50 mM KCl at 60° C. or conditions of equivalent stringency.

* * * * *

UNITED STATES PATENT AND TRADEMARK OFFICE
CERTIFICATE OF CORRECTION

PATENT NO.    : 5,795,735
DATED         : August 18, 1998
INVENTOR(S)   : Lockerbie et al.

It is certified that error appears in the above-identified patent and that said Letters Patent is hereby corrected as shown below:

Col. 5, line 40: Please delete "4 µjg", and insert - -4 µg- -.

Col. 5, line 46: Please delete "DIT", and insert --DTT--.

Col. 6, line 18: Please delete "Ht3", and insert - -Ht31- -.

Col. 8, line 42: Please delete "10 $^{32}$P-ATP", and insert - -10 µl $^{32}$P-ATP- -.

Col. 8, line 56: Please delete "T Cell)", and insert - -(T Cell)- -.

Col. 9, line 45: Please delete "trails", and insert - -trials- -.

Col. 9, line 58: Please delete "Sturrocketal", and insert - -Sturrock et al--.

Col. 9, line 58: Please delete "Nephrol. DiaL", and insert - -Nephrol. Dial.--

Col. 10, line 54: Please delete "J.Invest.Denn.", and insert --J.Invest.Derm--.

Col. 10, line 60: Please delete "Br.J.Dern", and insert--Br.J.Derm- -.

Col. 11, line 10: Please delete "IN one trail", and insert - -In one trial- -.

Col. 11, line 13: Please delete "J.Am.Acad.Denn.", and insert - -J.Am.Acad.Derm.--.

Col. 11, line 55: Please delete "FkS06", and insert - -Fk506--.

Col. 11, line 62: Please delete "8:483-385", and insert - -8:483-485- -.

UNITED STATES PATENT AND TRADEMARK OFFICE
CERTIFICATE OF CORRECTION

PATENT NO. : 5,795,735
DATED : August 18, 1998
INVENTOR(S) : Lockerbie, et. al.

It is certified that error appears in the above-identified patent and that said Letters Patent is hereby corrected as shown below:

Col. 11, line 66: Please delete "317:861-566", and insert - -317:861-866- -.

Col. 12, line 49: Please delete "trails", and insert - -trials- -.

Col. 13, line 16: Please delete "High does bolus", and insert --High dose bolus--.

Col. 14, line 38: Please delete "trails", and insert - -trials- -.

Signed and Sealed this

Twenty-fourth Day of October, 2000

Q. TODD DICKINSON

*Attest:*

*Attesting Officer*       *Director of Patents and Trademarks*